United States Patent [19]
Okamoto et al.

[11] Patent Number: 5,438,125
[45] Date of Patent: Aug. 1, 1995

[54] SIALIC ACID DERIVATIVES

[75] Inventors: Kaoru Okamoto; Shinji Morita, both of Hyogo, Japan

[73] Assignee: Nippon Zoki Pharmaceutical Co., Ltd., Osaka, Japan

[21] Appl. No.: 845,665

[22] Filed: Mar. 4, 1992

[30] Foreign Application Priority Data

Mar. 6, 1991 [JP] Japan .................. 3-068017

[51] Int. Cl.⁶ ................. C07H 15/00; C07H 15/24; C08B 37/00
[52] U.S. Cl. ........................... 536/4.1; 536/5; 536/6.1; 536/18.2; 536/18.7; 536/53; 536/55.1; 536/123; 530/395
[58] Field of Search ............. 536/53, 4.1, 18.7, 18.2, 536/55.1, 123, 5, 6.1; 530/395

[56] References Cited

U.S. PATENT DOCUMENTS

| | | | |
|---|---|---|---|
| 4,797,477 | 1/1989 | Yoshimura et al. | 536/53 |
| 4,990,603 | 2/1991 | Ogawa et al. | 536/4.1 |
| 5,023,239 | 6/1991 | Ogura et al. | 536/53 |
| 5,034,516 | 7/1991 | Roy et al. | 536/53 |
| 5,037,969 | 8/1991 | Minami et al. | 536/4.1 |
| 5,057,605 | 10/1991 | Yoshimura et al. | 536/4.1 |
| 5,077,397 | 12/1991 | Yoshimura et al. | 536/53 |

FOREIGN PATENT DOCUMENTS

| | | |
|---|---|---|
| 62-221694 | 9/1987 | Japan . |
| 62-292790 | 12/1987 | Japan . |
| 64-61493 | 3/1989 | Japan . |
| 2-202895 | 8/1990 | Japan . |
| 2-209885 | 8/1990 | Japan . |
| 2101588 | 1/1983 | United Kingdom . |

OTHER PUBLICATIONS

Laine et al; J. Biol. Chem. 249(14): 4460–4466 (1974).
Parikh et al; Methd. Enzymol. 34: 610–619 (1974).
Ponpipom et al; Can. J. Chem. 58:214–220 (1980).
Lindahl et al, Chemical Abstracts 107: 26512k (1987).
Levery et al; Carb. Res. 178: 121–144 (1988).
DeVries et al; Arch. Biochem. Biophys. 151: 243–250 (1972).
Okamoto et al; Tet. Lett. 27(43): 5229–5232 (1986).
Okamoto et al; Tet. Lett. 27(43): 5233–5236 (1986).
Okamoto et al; Bull. Chem. Soc. Jpn. 60: 637–643 (1987).
Okamoto et al; Tetrahedron 43(24): 5919–5928 (1987).
Okamoto et al; Tetrahedron 44(4): 1291–1298 (1988).
Paulsen et al; Liebigs, Ann. Chem. 3: 277–279 (1988).
Lee et al; Biol. Chem. Hoppe Seyler 371: 307–316 (Apr. 1990).

*Primary Examiner*—Douglas W. Robinson
*Assistant Examiner*—Howard C. Lee
*Attorney, Agent, or Firm*—Armstrong, Westerman, Hattori, McLeland & Naughton

[57] ABSTRACT

Sialic acid compounds of formula

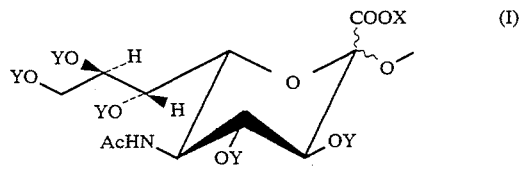

wherein X is hydrogen, a lower alkyl group or benzyl, Y is hydrogen or acetyl, Ac is acetyl, and the wavy line represents that the compound of the formula (I) includes both a α-anomer and β-anomer, have excellent chemical and enzymatical stability and are useful in the treatment of central or peripheral nervous diseases.

10 Claims, 2 Drawing Sheets

- ●—● R=H in H₂O at 80°C
- ○—○ R=OH in H₂O at 80°C
- ▲—▲ R=H in 0.01N H₂SO₄ at 80°C
- △—△ R=OH in 0.01N H₂SO₄ at 80°C

SIALIC ACID DERIVATIVES

BACKGROUND OF THE INVENTION

The present invention relates to novel sialic acid derivatives having excellent chemical and enzyme stability. The sialic acid derivatives are useful as medicines such as a drug for the treatment of central or peripheral nervous system diseases.

Sialic acids which are contained in ganglioside and glycoproteins exist in the surface of cells and bacteria. Recently, sialic acids become a subject of medical and pharmacological attention as a physiologically active substance which is involved in immunity, cancer, inflammation, virus infection, cell differentiation, hormone reception etc. Many compounds containing sialic acid have been synthesized, and it has been reported that the compounds have various pharmacological activities, for example, therapeutic effects on central or peripheral nervous system diseases and demyelinating diseases, inhibitory effect against cancer metastasis, and antiinflammatory effect.

The object of the present invention is to provide novel sialic acid derivatives having a hydroxy group at the 3-position, which are very stable chemically and enzymatically.

DETAILED DESCRIPTION OF THE INVENTION

Figure 1:
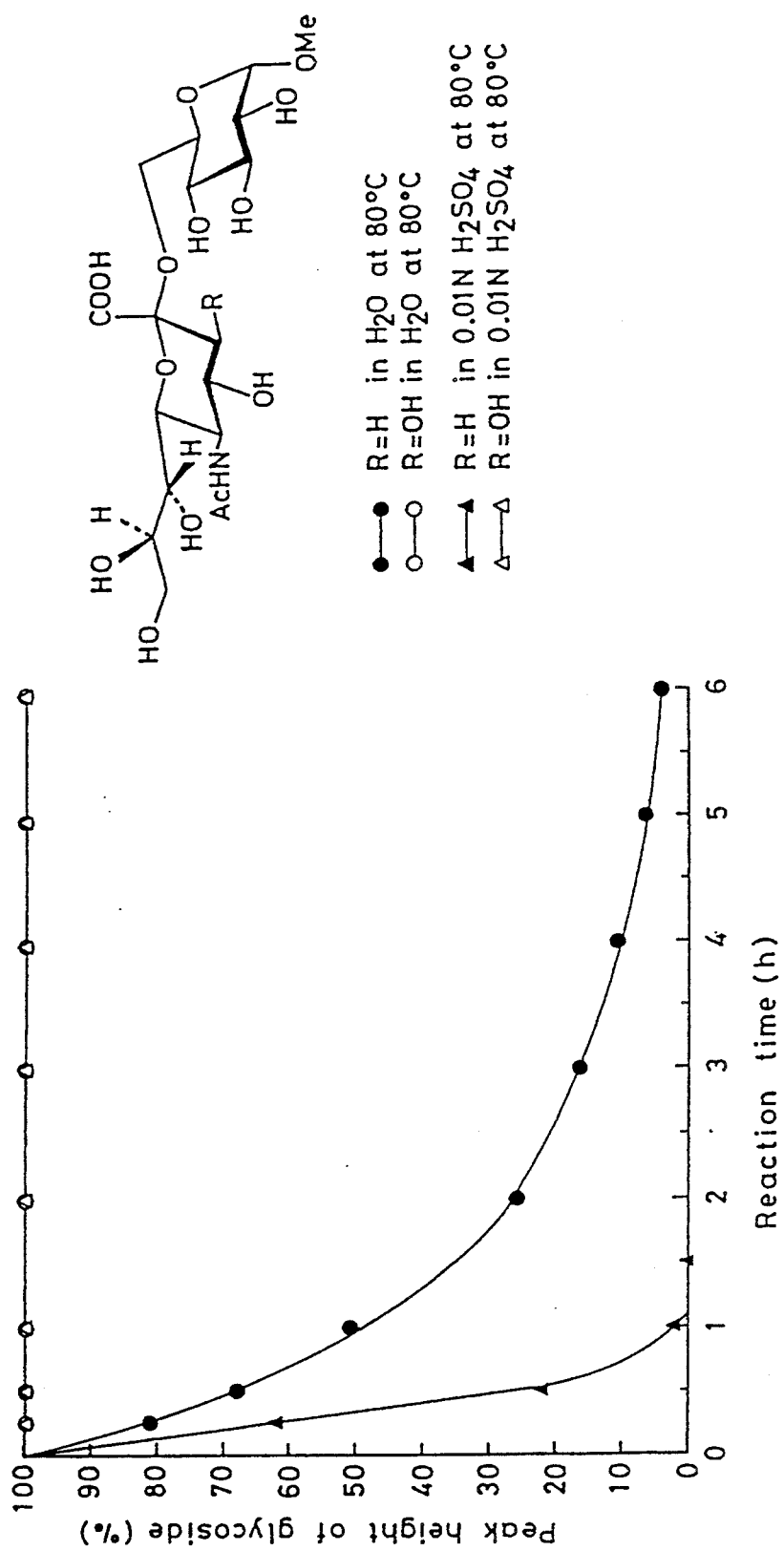
FIGS. 1 and 2 show the result of comparative tests on chemical stability.

The compounds of the present invention are sialic acid derivatives structurally containing a group represented by the following formula (I).

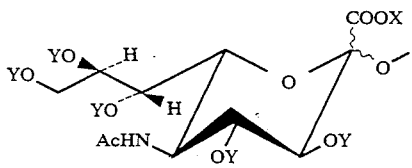

In the formula (I), X represents hydrogen, a lower alkyl group having 1 to 4 carbon atoms such as methyl, ethyl, n-propyl, iso-propyl, n-butyl, iso-butyl, sec-butyl, tert-butyl, or benzyl, Y represents hydrogen or acetyl, preferably hydrogen, and Ac represents acetyl. The wavy line represents that the said group of the formula (I) includes both the α-anomer and β-anomer.

Many compounds structurally containing sialic acid are naturally present and have been synthesized, for example, gangliosides, sialosylcholesterol, sialosylglycerolipids, sialosylceramides, etc. The sialic acid contained in these compounds is a normal sialic acid which has hydrogen atom at the 3-position. On the contrary, the sialic acid contained in the compounds of the present invention has a hydroxy group at the 3-position, and so the compounds structurally containing 3-hydroxy sialic acid are novel.

The compounds of the present invention include all of sialic acid derivatives containing a group of formula (I). For example, the compounds of the present invention may be represented by the following formula (II)

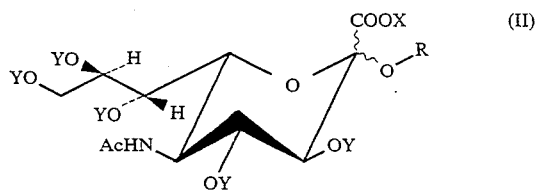

In formula (II), X, Y and Ac represent the same groups as in formula (I), and R represents for example, alkyl, aryl, monosaccharide such as glucose, galactose, mannose fucose, glucosamine, galactosamine, N-acetylglucosamine, N-acetylgalactosamine or sialic acid, oligosaccharides comprising those monosaccharides, sphingoglycolipids such as cerebrosides or gangliosides, glycolipids such as glyceroglycolipids, ceramides, glycoproteins containing the said saccharides, steroids such as cholesterols, glycerolipids such as alkylglycerols, dialkylglycerols, alkylacylglycerols or diacylglycerols, natural nucleoside such as adenosine, guanosine, inosine, cytidine or uridine, modified nucleosides such as azidothymidine, purine bases such as adenine or guanine, pyrimidine bases such as cytosine, thymine or uracil, or modified bases such as acyclovir or 5-fluorouracil.

The sialic acid derivatives of the present invention include pharmaceutically acceptable salts of the compounds having formula (I) above, for example, salts as acid addition salts with an acid such as hydrochloric acid, sulfuric acid, nitric acid, phosphoric acid, formic acid, acetic acid, citric acid or lactic acid, salts with alkali metal such as sodium or potassium, salts with alkaline earth metal such as calcium, magnesium or barium, or salts with other metals such as aluminum. These salts can be produced from free sialic acid derivatives in the usual way or can be interchanged with each other.

When optical isomers exist in the compounds of the invention, the present invention includes any types of isomers.

The sialic acid derivatives of the present invention can be prepared as indicated below.

The compounds of the present invention can be prepared by a glycosidation reaction in which alkyl or benzyl esters of 5-acetamide-4,7,8,9-tetra-O-acetyl-2-halogeno-2,5-dideoxy-β-D-erythro-L-gluco-2-nonulopyranosonate are used as the glycosidation donor. As the alkyl esters, a lower alkyl ester having 1 to 4 carbon atoms, such as methyl, ethyl, n-propyl, iso-propyl, n-butyl, iso-butyl, sec-butyl and t-butyl, can be employed. The halogen group of the donor at 2-position is flourine, chlorine, bromine or iodine, and bromine is preferable. As the glycosidation acceptor reacted with the donor, a compound having at least one hydroxy group, which is represented by the general formula R—OH, wherein R represents the same group as mentioned above in formula (II), can be employed.

The glycosidation can be carried out under the reaction conditions indicated below.

An appropriate solvent which does not inhibit the reaction, such as toluene, benzene or a mixed solvent of toluene and 1,2-dichloroethane, can be employed. Silver trifluoromethanesulfonate is preferred catalyst. As a neutralizer, an alkali salt of phosphoric acid, such as sodium phosphate or potassium phosphate, or silver carbonate is preferably employed. The ratio of α- anomer and β-anomer produced varies according to the temperature of the reaction. An excessively long reaction time sometimes causes decomposition of the product by side reactions. Therefore, a reaction time of about from 5 minutes to an hour is sufficient to avoid the occurrence of a side reaction.

In addition, the β-anomer of the compound of the present invention can be selectively prepared by the glycosidation in which alkyl or benzyl esters of 5-acetamide-4,7.8.9-tetra-O-acetyl-2,3-anhydro-5-deoxy-β-D-erythro-L-gluco-2-nonulopyranosonate are used as the glycosidation donor. The same group of the alkyl esters as mentioned above can be employed. Also the reaction conditions, such as solvent, catalyst, etc., can be chosen as described above. The donor in this glycosidation and the preparation thereof are described in the published paper [Okamoto et al., Bull. Chem. Soc. Jpn., 60, 631–636 (1987)].

Deacetylation after glycosidation can be carried out by conventional methods, for example, deacetylation is carried out in an appropriate solvent such as methanol or ethanol in the presence of a basic catalyst, such as, alkaline metal alkoxide, for example, potassium t-butoxide or sodium methoxide.

There are many cases that groups of the glycosidation acceptor, except for the hydroxy group reacting with the donor, should be protected. For example, when glucose is used as the acceptor, the hydroxy groups of glucose, which are not reacted with a donor, are preferably protected with a benzyl group. Also other acceptors can be protected by appropriate protecting groups, and deprotection can be carried out by conventional methods. For example, the benzyl group can be removed by contact catalytic reduction in the presence of palladium-carbon in an appropriate solvent such as methanol or the like.

The sialic acid derivatives of the present invention, in which the group X is a lower alkyl or benzyl, can be easily converted to the compounds, in which the group X is hydrogen, by a conventional method such as hydrolysis.

The resulting compounds of the present invention can be purified by known methods such as distillation, chromatography and recrystallization. Identification is established through, inter alia, melting point, elemental analysis, TLC, IR, NMR, UV, mass spectrum, etc. The specific rotation was measured using sodium lump ($\lambda = 5893$ Å).

EXAMPLE

Example 1

(1) 6.6 g of methyl 5-acetamido-4,7,8,9-tetro-O-acetyl-2-bromo-2,5-dideoxy-β-D-erythro-L-gluco-2-nonulopyranosonate (Compound A). 5.0 g of 5-cholesten-3β-ol, 6.6 g of anhydrous disodium hydrogenphosphate and 140 ml of dry benzene were mixed and stirred. 3.1 g of silver trifluoromethanesulfonate in 90 ml of dry benzene was added at room temperature under argon atmosphere. After stirring for 10 minutes, the reaction mixture was filtered to remove the insoluble material and washed with ethyl acetate. The combined filtrate and washings were washed with 5% $Na_2S_2O_3$, 5% $NaHCO_3$ and brine, and evaporated to give a syrup. The crude product was purified by silica gel column chromatography to give methyl (5-cholesten-3β-yl 5-acetamido-4,7,8,9-tetra-O-acetyl-5-deoxy-D-erythro-L-gluco-2-nonulopyranosid)oate as a mixture of α-anomer and β-anomer ($\alpha:\beta = 6:1$).

Recovery: 61%

| Elementary Analysis: $C_{47}H_{73}NO_{14}$ | | | |
|---|---|---|---|
| | C % | H % | N % |
| Calculated | 64.44 | 8.40 | 1.60 |
| Found | 64.72 | 8.34 | 1.88 |

(2) 2.2 g of the said product and a catalytic amount of potassium t-butoxide were dissolved in 100 ml of absolute methanol and stirred for an hour at room temperature under argon atmosphere. The reaction mixture was neutralized with cation exchanged resin and the resin was filtered and washed with methanol. The combined filtrate and washings were evaporated in vacuo and the solid residue was recrystalized from a mixture of chloroform, methanol and ether to give α-anomer of methyl (5-cholesten-3β-yl 5-acetamido-5-deoxy-D-erythro-L-gluco-2-nonulopyranosid)onate as white crystals. After condensing the filtrate of recrystalization, the residue was purified by silica gel column to separate β-anomer and the remaining α-anomer.

[α-anomer]

Recovery: 80% m.p.: 229°–231° C. $[\alpha]^{25}$: $-23.7°$ (c=0.65, chloroform/methanol=5/1) IR (KBr): 3470, 3400, 2950, 1730, 1620, 1548, 1435, 1373, 1315, 1070, 1033 $cm^{-1}$ Mass (SIMS): m/z 708 (M+H), 322 (M-cholesterol+1)

| Elementary Analysis: $C_{39}H_{65}NO_{10}$ | | | |
|---|---|---|---|
| | C % | H % | N % |
| Calculated | 66.17 | 9.25 | 1.98 |
| Found | 66.17 | 9.51 | 2.04 |

$^1$H-NMR ($CDCl_3/CD_3OD = 1/1$, δ) cholesterol moiety 0.69(s,3H), 0.87 and 0.88(2d,J=6.6 Hz,2×3H), 0.93(d,J=6.4 Hz,3H), 1.00(s,3H), 3.68–3.75(m,1H), 5.31–5.35(m,1H); Neu5Ac moiety 2.05(s,3H), 3.47(dd,J=1.2, 8.4 Hz,1H), 3.61(d,J=9.1 Hz,1H), 3.77(dd,J=8.2, 9.1 Hz,1H), 3.81(s,3H), 3.93(dd,J=1.2, 8.2 Hz,1H), 3.96(dd,J=8.2, 8.2 Hz,1H)

[β-anomer]

Recovery: 13% m.p.: 272°–275° C. $[\alpha]^{25}$: $-53.7°$ (c=0.51, chloroform/methanol=5/1) IR (KBr): 3420, 2920, 1740, 1614, 1570, 1430, 1380, 1315, 1095, 1024 $cm^{-1}$ Mass (SIMS): m/z 708 (M+H), 322 (M-cholesterol+1)

| Elementary Analysis: $C_{39}H_{65}NO_{10}$ | | | |
|---|---|---|---|
| | C % | H % | N % |
| Calculated | 66.17 | 9.25 | 1.98 |
| Found | 66.23 | 9.69 | 1.84 |

$^1$H-NMR ($CDCl_3/CD_3OD=1/1$, δ) cholesterol moiety 0.69 (s,3H), 0.86 and 0.87(2d,J=6.6 Hz,2×3H), 0.93 (d,J=6.5 Hz,3H), 1.01(s,3H), 3.65–3.74 (m,1H), 5.25–5.29(m,1H); Neu5Ac moiety 2.04 (s,3H), 3.44(dd,J=0.5, 8.8 Hz,1H), 3.55(d,J=9.0 Hz,1H), 3.83(s,3H), 3.84(dd,J=9.0, 9.1 Hz,1H), 3.92(dd,J=0.5, 8.5 Hz,1H), 3.95(dd,J=8.5, 9.1 Hz,1H)

(3) 1.2 g of the said α-anomer, 10 ml of 1N NaOH and 200 ml of methanol were mixed and stirred for 2 hours at room temperature. After neutralizing with cation exchange resin, the resin was filtered and washed with methanol. The combined filtrate and washings were condensed to give a solid, which was washed with ether and recrystalized from a mixture of methanol, chloroform and hexane to give 5-cholesten-3β-yl 5-acetamido-5-deoxy-α-D-erythro-L-gluco-2-nonulopyranosidonic acid (Compound 1α) as a white crystal.

Recovery: 97% m.p.: 191°-193° C. $[\alpha]^{25}$: 21.4° (c=0.53, chloroform/methanol=1/1) IR (KBr): 3250, 2945, 1715, 1620, 1560, 1460, 1368, 1103, 1066, 1021 $cm^{-1}$ Mass (SIMS): m/z 694 (M+H), 308 (M-cholesterol+1)

| Elementary Analysis: $C_{38}H_{63}NO_{10}$ | | | |
|---|---|---|---|
| | C % | H % | N % |
| Calculated | 65.77 | 9.15 | 2.02 |
| Found | 65.59 | 9.61 | 2.13 |

$^1$H-NMR (CD$_3$OD, δ) cholesterol moiety 0.71(s,3H), 0.87 and 0.88(2d,J=6.5 Hz,2×3H), 0.94(d,J=6.4 Hz,3H), 1.02(s,3H), 3.67-3.76(m,1H), 5.33-5.37(m,1H); Neu5Ac moiety 2.02(s,3H), 3.49(dd,J=1.5, 8.7 Hz,1H), 3.56(d,J=9.5 Hz,1H), 3.64(dd,$^J$=6.3, 12.1 Hz,1H), 3.70(dd,J=9.5, 10.2 Hz,1H), 3.81(dd,J=12.1 Hz,1H), 3.82(dd,J=1.5, 10.3 Hz,1H), 3.82(ddd,J=6.3, 8.7 Hz,1H), 3.93(dd,J=10.2, 10.3 Hz,1H)

In the same manner as described above, the β-anomer, 5-cholesten-3β-yl 5-acetamido-5-deoxy-β-D-erythro-L-gluco-2-nonulopyranosidonic acid (Compound 1β), was obtained.

Recovery: 97% m.p.: 193°-195° C. $[\alpha]^{25}$: −56.9° (c=0.54, chloroform/methanol=1/1) IR (KBr): 3400, 3260, 2920, 1757, 1618, 1578, 1375, 1160, 1085, 1020 $cm^{-1}$ Mass (SIMS): m/z 694 (M+H), 308 (M-cholesterol+1)

| Elementary Analysis: $C_{38}H_{63}NO_{10}$ | | | |
|---|---|---|---|
| | C % | H % | N % |
| Calculated | 65.77 | 9.15 | 2.02 |
| Found | 65.64 | 9.55 | 1.93 |

$^1$H-NMR (CD$_3$OD, δ) cholesterol moiety 0.71(s,3H), 0.87 and 0.88(2d,J=6.6 Hz,2×3H), 0.94(d,J=6.5 Hz,3H), 1.02(s,3H), 3.73-3.81(m,1H), 5.26-5.31(m,1H); Neu5Ac moiety 2.00(s,3H), 3.43(d,J=9.1 Hz,1H), 3.48(dd,J=0.5, 9.0 Hz,1H), 3.64(dd,J=4.8, 11.0 Hz,1H), 3.75(ddd,J=2.5, 4.8, 9.0 Hz,1H), 3.79(dd,J=2.5, 11.0 Hz,1H), 3.85(dd,J=9.1, 9.2 Hz,1H), 3.96(dd,J=8.5, 9.2 Hz, 1H), 3.99(dd,J=0.5, 8.5Hz,1H)

Example 2

Compound A, a starting material, was glycosidated with methyl 2,3,4,-tri-O-benzyl-α-D-glucoside in the presence of silver trifluoromethanesulfonate in the same manner as Example 1(1). Each of obtained α-anomer and β-anomer was deacetylated in the same manner as Example 1(2), and then debenzylated by contact reduction according to a usual manner. After hydrolysis of methyl ester in the same manner as Example 1(3), it was neutralized with cation exchange resin to give the following compounds.

Methyl 6-O-(5-acetamido-5-deoxy-α-D-erythro-L-gluco-2-nonulopyranosylonate)-α-D-glucopyranoside (Compound 2α).

m.p.: 85°14 87° C. $[\alpha]^{25}$: +26.8° (c=1.1, H$_2$O) IR (KBr): 3350, 1735, 1640, 1555, 1370, 1030 $cm^{-1}$ Mass (SIMS): m/z 502 (M+H), 308 (M-Glc)

| Elementary Analysis: $C_{18}H_{31}NO_{15}.3H_2O$ | | | |
|---|---|---|---|
| | C % | H % | N % |
| Calculated | 38.92 | 6.71 | 2.52 |
| Found | 38.70 | 6.55 | 2.73 |

$^1$H-NMR (D$_2$O/ TSP, δ) Glc moiety 3.41(s,3H), 3.47(dd,J=9.2, 9.3 Hz,1H), 3.56(dd,J=3.7, 9.8 Hz,1H), 3.64(dd,J=9.2, 9.8 Hz,1H), 3.76(ddd,J=9.3Hz,1H), 3.98(m,2H), 4.78(d,J=3.7 Hz,1H); Neu5Ac moiety 2.03(s,3H)

Methyl 6-O-(5-acetamido-5-deoxy-β-D-erythro-L-gluco-2-nonulopyranosylonate)-α-D-glucopyranoside (Compound 2β).

m.p.: 79°-81° C. $[\alpha]^{25}$: +17.7° (c=1.1, H$_2$O ) IR (KBr): 3400, 1730, 1635, 1550, 1368, 1070, 1028 $cm^{-1}$ Mass (SIMS): m/z 502 (M+H), 524 (M+Na), 308 (M-Glc)

| Elementary Analysis: $C_{18}H_{31}NO_{15}.2H_2O$ | | | |
|---|---|---|---|
| | C % | H % | N % |
| Calculated | 40.22 | 6.50 | 2.61 |
| Found | 40.67 | 6.96 | 2.41 |

$^1$H-NMR (D$_2$O/TSP, δ) Glc moiety 3.41(s,3H), 3.61(dd,J=3.8, 8.9 Hz,1H), 3.77(ddd,J=1.3, 3.5 Hz,1H), 3.85(dd,J=3.5, 10.6 Hz,1H), 3.92(dd,J=1.3, 10.6 Hz,1H), 4.81(d,J=3.8 Hz,1H); Neu5Ac moiety 2.05(s,3H), 3.54(d,J=9.1 Hz,1H). 3.83(m,1H), 3.84(d,J=9.8 Hz,1H), 3.90(dd,J=9.8, 10.3 Hz,1H) 3.98(d,J=10.6 Hz,1H), 4.06(dd, J=10.3, 10.6 Hz,1H)

Example 3

Compound A, a starting material, was glycosidated with 1,2 (or 2,3)-di-O-alkyl-sn-glycerol in the presence of silver trifluoromethanesulfonate in the same manner as Example 1(1) to give a mixture of α-anomer and β-anomer. It was impossible to separate both anomers by silica gel chromatography. But the both anomers could be separated by silica get column chromatography by benzoylation of hydroxy group at 3-position at room temperature in the treatment with pyridine and benzoyl chloride under argon atmosphere. The separated α-anomer and β-anomer were deacylated by Zemplen method according to a usual manner. After hydrolysis of methyl ester in the same manner as Example 1(3), it was neutralized with cation exchange resin to give the following compounds.

3-O-(5-acetamido-5-deoxy-α-D-erythro-L-gluco-2-nonulopyranosylonic acid)-1,2-di-O-octyl-sn-glycerol (Compound 3α).

3-O-(5-acetamido-5-deoxy-β-D-erythro-L-gluco-2-nonulopyranosylonic acid)-1,2-di-O-octyl-sn-glycerol (Compound 3β).

3-O-(5-acetamido-5-deoxy-α-D-erythro-L-gluco-2-nonulopyranosylonic acid)-1,2-di-O-decyl-sn-glycerol (Compound 4α).

3-O-(5-acetamido-5-deoxy-β-D-erythro-L-gluco-2-nonulopyranosylonic acid)-1,2-di-O-decyl-sn-glycerol (Compound 4β).

3-O-(5-acetamido-5-deoxy-α-D-erythro-L-gluco-2-nonulopyranosylonic acid)-1,2-di-O-dodecyl-sn-glycerol (Compound 5α).

3-O-(5-acetamido-5-deoxy-β-D-erythro-L-gluco-2-nonulopyranosylonic acid)-1,2-di-O-dodecyl-sn-glycerol (Compound 5β).

3-O-(5-acetamido-5-deoxy-α-D-erythro-L-gluco-2-nonulopyranosylonic acid)-1,2-di-O-tetradecyl-sn-glycerol (Compound 6α).

3-O-(5-acetamido-5-deoxy-β-D-erythro-L-gluco-2-nonulopyranosylonic acid)-1,2-di-O-tetradecyl-sn-glycerol (Compound 6β).

3-O-(5-acetamido-5-deoxy-α-D-erythro-L-gluco-2-nonulopyranosylonic acid)-1,2-di-O-hexadecyl-sn-glycerol (Compound 7α).

3-O-(5-acetamido-5-deoxy-β-D-erythro-L-gluco-2-nonulopyranosylonic acid)-1,2-di-O-hexadecyl-sn-glycerol (Compound 7β).

3-O-(5-acetamido-5-deoxy-α-D-erythro-L-gluco-2-nonulopyranosylonic acid)-1,2-di-O-octadecyl-sn-glycerol (Compound 8α).

3-O-(5-acetamido-5-deoxy-β-D-erythro-L-gluco-2-nonulopyranosylonic acid)-1,2-di-O-octadecyl-sn-glycerol (Compound 8β).

1-O-(5-acetamido-5-deoxy-α-D-erythro-L-gluco-2-nonulopyranosylonic acid)-2,3-di-O-tetradecyl-sn-glycerol (Compound 9α).

1-O-(5-acetamido-5-deoxy-β-D-erythro-L-gluco-2-nonulopyranosylonic acid)-2,3-di-O-tetradecyl-sn-glycerol (Compound 9β).

3-O-(5-acetamido-5-deoxy-α-D-erythro-L-gluco-2-nonulopyranosylonic acid)-1,2-di-O-tetradecyl-rac-glycerol (Compound 10α).

3-O-(5-acetamido-5-deoxy-β-D-erythro-L-gluco-2-nonulopyranosylonic acid)-1,2-di-O-tetradecyl-rac-glycerol (Compound 10β).

3-O-(5-acetamido-5-deoxy-α-D-erythro-L-gluco-2-nonulopyranosylonic acid)-1-O-dodecyl-2-O-tetradecyl-sn-glycerol (Compound 11α).

3-O-(5-acetamido-5-deoxy-β-D-erythro-L-gluco-2-nonulopyranosylonic acid)-1-O-dodecyl-2-O-tetradecyl-sn-glycerol (Compound 11β).

3-O-(5-acetamido-5-deoxy-α-D-erythro-L-gluco-2-nonulopyranosylonic acid )-2-O-dodecyl-1-O-tetradecyl-sn-glycerol (Compound 12α).

3-O-(5-acetamido-5-deoxy-β-D-erythro-L-gluco-2-nonulopyranosylonic acid )-2-O-dodecyl-1-O-tetradecyl-sn-glycerol (Compound 12β).

The physical data of the said compound obtained in Example 3 were shown in Tables 1 and 2.

Example 4

Compound A, a starting material, was glycosidated with 3-O-alkyl-sn-glycerol in the presence of silver trifluoromethanesulfonate to give a mixture of α-anomer and β-anomer. It was impossible to separate both anomers by silica gel chromatography. The both anomers could be separated by silica gel chromatography by intramolecular lactonation in the treatment with 4-dimethylaminopyridine in acetonitril. The separated α-amomer and β-anomer were deacylated by Zemplen method according to a usual manner. After hydrolysis of methyl ester in the same manner as Example 1(3), it was neutralized with cation exchange resin to give the following compounds.

1-O-(5-acetamido-5-deoxy-α-D-erythro-L-gluco-2-nonulopyranosylonic acid)-3-O-dodecyl-sn-glycerol (Compound 13α).

1-O-(5-acetamido-5-deoxy-β-D-erythro-L-gluco-2-nonulopyranosylonic acid)-3-O-dodecyl-sn-glycerol (Compound 13β).

1-O-(5-acetamido-5-deoxy-α-D-erythro-L-gluco-2-nonulopyranosylonic acid)-3-O-tetradecyl-sn-glycerol (Compound 14α).

1-O-(5-acetamido-5-deoxy-β-D-erythro-L-gluco-2-nonulopyranosylonic acid)-3-O-tetradecyl-sn-glycerol (Compound 14β).

1-O-(5-acetamido-5-deoxy-α-D-erythro-L-gluco-2-nonulopyranosylonic acid)-3-O-hexadecyl-sn-glycerol (Compound 15α).

1-O-(5-acetamido-5-deoxy-β-D-erythro-L-gluco-2-nonulopyranosylonic acid)-3-O-hexadecyl-sn-glycerol (Compound 15β).

1-O-(5-acetamido-5-deoxy-α-D-erythro-L-gluco-2-nonulopyranosylonic acid)-3-O-octadecyl-sn-glycerol (Compound 16α).

1-O-(5-acetamido-5-deoxy-β-D-erythro-L-gluco-2-nonulopyranosylonic acid)-3-O-octadecyl-sn-glycerol (Compound 16β).

1-O-(5-acetamido-5-deoxy-α-D-erythro-L-gluco-2-nonulopyranosylonic acid)-3-O-icosyl-sn-glycerol (Compound 17α).

1-O-(5-acetamido-5-deoxy-α-D-erythro-L-gluco-2-nonulopyranosylonic acid)-3-O-icosyl-sn-glycerol (Compound 17β).

1-O-(5-acetamido-5-deoxy-α-D-erythro-L-gluco-2-nonulopyranosylonic acid)-3-O-docosyl-sn-glycerol (Compound 18α).

1-O-(5-acetamido-5-deoxy-β-D-erythro-L-gluco-2-nonulopyranosylonic acid)-3-O-docosyl-sn-glycerol (Compound 18β).

The physical data of the said compound obtained in Example 4 were shown in Table 3.

Example 5.

After compound A was glycosidated with alkylalcohol, deacetylation and hydrolysis of methyl ester were carried out in the same manner as Example 1. In this reaction, α-anomer was highly synthesized to give the following compounds.

Tetradecyl 5-acetamido-5-deoxy-α-D-erythro-L-gluco-2-nonulopyranosylonic acid (Compound 19α).

Hexadecyl 5-acetamido-5-deoxy-α-D-erythro-L-gluco-2-nonulopyranosylonic acid (Compound 20α).

Example 6

Compound A was glycosidated with 2',3'-Di-O-tert-butyldimethylsilyluridine in the same manner as Example 1(1). After the resulting α-anomer and β-anomer were acetylated by treatment with anhydrous acetic acid in pyridine, the both anomers were separated by silica gel chromatography. The separated α-amomer and β-anomer were deacylated by Zemplen method according to a usual manner, and desilylated by the treatment with n-Bu4NF. Then hydrolysis of methyl ester was carried out in the same manner as Example 1(3) to give the following compounds.

5'-O-(5-acetamido-5-deoxy-α-D-erythro-L-gluco-2-nonulopyranosylonic acid)-uridine (Compound 21α).

5'-O-(5-acetamido-5-deoxy-β-D-erythro-L-gluco-2-nonulopyranosylonic acid)-uridine (Compound 21β).

Example 7

(1) 1.0 g of Compound 1α was suspended in 100 ml of ethanol, and sodium hydrogen carbonate (121 mg) in water (10 ml) was added thereto at room temperature. The mixture became clear after stirring for 0.5 hr and condensed to give a syrup. The syrup was dissolved in 100 ml of water and filtered through a micro filter. The filtrate was condensed and dried to give sodium (5-cholesten-3β-yl 5-acetamido-5-deoxy-α-D-erythro-L-gluco-2-nonulopyranosid)onate (Compound 22α) as an amorphous powder.

Recovery: 95% m.p.: 201°–205° C. $[\alpha]^{25}$: −14.9° (c=0.2, $CH_3OH$) IR (KBr): 3380, 2930, 1615, 1555, 1460, 1430, 1378, 1270, 1112, 1072, 1020 $cm^{-1}$ Mass (SIMS): m/z 716 (M+Na)

| Elementary Analysis: $C_{38}H_{62}NO_{10}Na$ | | | |
|---|---|---|---|
| | C % | H % | N % |
| Calculated | 63.75 | 8.73 | 1.96 |
| Found | 63.55 | 9.01 | 1.94 |

$^1$H-NMR ($CD_3OD$, δ) cholesterol moiety 0.70(s,3H), 0.87 and 0.88(2d,J=6.6 Hz,2×3H), 0.93(d,J=6.5 Hz,3H), 1.00(s,3H), 3.83–3.90(m,1H), 5.33–5.39(m,1H); Neu5Ac moiety 2.04(s,3H), 3.37(d,J=9.6 Hz,1H), 3.52(dd,J=1.7, 8.9 Hz,1H), 3.54(dd,J=9.6, 9.6 Hz,1H), 3.58(dd,J=1.7, 10.5 Hz,1H), 3.66(dd,J=5.2, 11.4 Hz,1H), 3.81(dd,J=9.6, 10.5 Hz,1H), 3.84(dd,J=2.5, 11.4 Hz,1H), 3.88(ddd,J=2.5, 5.2, 8.9 Hz,1H)

(2) Instead of Compound 1α, Compound 1β was used in the same manner to give sodium (5-cholesten-3β-yl 5acetamido-5-deoxy-β-D-erythro-L-gluco-2-nonulopyranosid)onate (Compound 22β)

Recovery: 92% m.p.: 226°–229° C. $[\alpha]^{25}$: −51.8° (c=0.5, $CH_3OH$) IR (KBr): 3400, 2925, 1618, 1550, 1460, 1430, 1375, 1160, 1063, 1030 $cm^{-1}$ Mass (SIMS): m/z 716 (M+Na)

| Elementary Analysis: $C_{38}H_{62}NO_{10}Na$ | | | |
|---|---|---|---|
| | C % | H % | N % |
| Calculated | 63.75 | 8.73 | 1.96 |
| Found | 63.66 | 8.68 | 2.11 |

$^1$H-NMR ($CD_3OD$, δ) cholesterol moiety 0.71(s,3H), 0.87 and 0.88(2d,J=6.5 Hz,2×3H), 0.93(d,J=6.4 Hz,3H), 1.00(s,3H), 3.65–3.72(m,1H), 5.27–5.32(m,1H); Neu5Ac moiety 1.97(s,3H), 3.37(d,J=9.3 Hz,1H), 3.39(dd,J=0.5, 9.1 Hz,1H), 3.66(dd,J=4.7, 11.4 Hz,1H), 3.77(ddd,J=3.0, 4.7, 9.1 Hz,1H), 3.80(dd,J=3.0, 11.4 Hz,1H), 3.85(dd,J=9.3, 9.5 Hz,1H), 3.97(dd,J=0.5, 9.8 Hz, 1H ), 4.03(dd,J=9.5, 9.8 Hz,1H)

(3) The compounds obtained in Examples 3, 4, 5 and 6, i.e. from Compound 3α to Compound 21β, were treated In the same manner as described above to give the following compounds.

3-O-[sodium (5-acetamido-5-deoxy-α-D-erythro-L-gluco-2-nonulopyranosyl)onate]-1,2-di-O-octyl-sn-glycerol (Compound 23α).

3-O-[sodium (5-acetamido-5-deoxy-β-D-erythro-L-gluco-2-nonulopyranosyl)onate]-1,2-di-O-octyl-sn-glycerol (Compound 23β).

3-O-[sodium (5-acetamido-5-deoxy-α-D-erythro-L-gluco-2-nonulopyranosyl)onate]-1,2-di-O-decyl-sn-glycerol (Compound 24α).

3-O-[sodium (5-acetamido-5-deoxy-α-D-erythro-L-gluco-2-nonulopyranosyl)onate]-1,2-di-O-decyl-sn-glycerol (Compound 24β).

3-O-[sodium (5-acetamido-5-deoxy-a-D-erythro-L-gluco-2-nonulopyranosyl)onate]-1,2-di-O-dodecyl-sn-glycerol (Compound 25β).

3-O-[sodium (5-acetamido-5-deoxy-α-D-erythro-L-gluco-2-nonulopyranosyl)onate]-1,2-di-O-dodecyl-sn-glycerol (Compound 25β).

3-O-[sodium (5-acetamido-5-deoxy-α-D-erythro-L-gluco-2-nonulopyranosyl)onate]-1,2-di-O-tetradecyl-sn-glycerol (Compound 26α).

3-O-[sodium (5-acetamido-5-deoxy-β-D-erythro-L-gluco-2-nonulopyranosyl)onate]-1,2-di-O-tetradecyl-sn-glycerol (Compound 26β).

3-O-[sodium (5-acetamido-5-deoxy-α-D-erythro-L-gluco-2-nonulopyranosyl)onate]-1,2-di-O-hexadecyl-sn-glycerol (Compound 27α).

3-O-[sodium (5-acetamido-5-deoxy-β-D-erythro-L-gluco-2-nonulopyranosyl)onate]-1,2-di-O-hexadecyl-sn-glycerol (Compound 27β).

3-O-[sodium (5-acetamido-5-deoxy-β-D-erythro-L-gluco-2-nonulopyranosyl)onate]-1,2-di-O-octadecyl-sn-glycerol (Compound 28α).

3-O-[sodium (5-acetamido-5-deoxy-β-D-erythro-L-gluco-2-nonulopyranosyl)onate]-1,2-di-O-octadecyl-sn-glycerol (Compound 28β).

1-O-[sodium (5-acetamido-5-deoxy-α-D-erythro-L-gluco-2-nonulopyranosyl)onate]-2,3-di-O-tetradecyl-sn-glycerol (Compound 29α).

1-O-[sodium (5-acetamido-5-deoxy-β-D-erythro-L-gluco-2-nonulopyranosyl)onate]-2,3-di-O-tetradecyl-sn-glycerol (Compound 29β).

3-O-[sodium (5-acetamido-5-deoxy-α-D-erythro-L-gluco-2-nonulopyranosyl)onate]-1,2-di-O-tetradecyl-rac-glycerol (Compound 30α).

3-O-[sodium (5-acetamido-5-deoxy-β-D-erythro-L-gluco-2-nonulopyranosyl)onate]-1,2-di-O-tetradecyl-rac-glycerol (Compound 30β).

3-O-[sodium (5-acetamido-5-deoxy-α-D-erythro-L-gluco-2-nonulopyranosyl)onate]-1-O-dodecyl-2-O-tetradecyl-sn-glycerol (Compound 31α).

3-O-[sodium (5-acetamido-5-deoxy-β-D-erythro-L-gluco-2-nonulopyranosyl)onate]-1-O-dodecyl-2-O-tetradecyl-sn-glycerol (Compound 31β).

3-O-[sodium (5-acetamido-5-deoxy-α-D-erythro-L-gluco-2-nonulopyranosyl)onate]-2-O-dodecyl-1-O-tetradecyl-sn-glycerol (Compound 32α).

3-O-[sodium (5-acetamido-5-deoxy-β-D-erythro-L-gluco-2-nonulopyranosyl)onate]-2-O-dodecyl-1-O-tetradecyl-sn-glycerol (Compound 32β).

1-O-[sodium (5-acetamido-5-deoxy-α-D-erythro-L-gluco-2-nonulopyranosyl)onate]-3-O-dodecyl-sn-glycerol (Compound 33α).

1-O-[sodium (5-acetamido-5-deoxy-α-D-erythro-L-gluco-2-nonulopyranosyl)onate]-3-O-dodecyl-sn-glycerol (Compound 33β).

1-O-[sodium (5-acetamido-5-deoxy-α-D-erythro-L-gluco-2-nonulopyranosyl)onate]-3-O-tetradecyl-sn-glycerol (Compound 34α).

1-O-[sodium (5-acetamido-5-deoxy-β-D-erythro-L-gluco-2-nonulopyranosyl)onate]-3-O-tetradecyl-sn-glycerol (Compound 34Γ).

1-O-[sodium (5-acetamido-5-deoxy-α-D-erythro-L-gluco-2-nonulopyranosyl)onate]-3-O-hexadecyl-sn-glycerol (Compound 35α).

1-O-[sodium (5-acetamido-5-deoxy-β-D-erythro-L-gluco-2-nonulopyranosyl)onate]-3-O-hexadecyl-sn-glycerol (Compound 35β).

1-O-[sodium (5-acetamido-5-deoxy-α-D-erythro-L-gluco-2-nonulopyranosyl)onate]-3-O-octadecyl-sn-glycerol (Compound 36α).

1-O-[sodium (5-acetamido-5-deoxy-β-D-erythro-L-gluco-2-nonulopyranosyl)onate]-3-O-octadecyl-sn-glycerol (Compound 36β).

1-O-[sodium (5-acetamido-5-deoxy-α-D-erythro-L-gluco-2-nonulopyranosyl)onate]-3-O-icosyl-sn-glycerol (Compound 37α).

1-O-[sodium (5-acetamido-5-deoxy-β-D-erythro-L-gluco-2-nonulopyranosyl)onate]-3-O-icosyl-sn-glycerol (Compound 37β).

1-O-[sodium (5-acetamido-5-deoxy-α-D-erythro-L-gluco-2-nonulopyranosyl)onate]-3-O-docosyl-sn-glycerol (Compound 38α).

1-O-[sodium (5-acetamido-5-deoxy-β-D-erythro-L-gluco-2-nonulopyranosyl)onate]-3-O-docosyl-sn-glycerol (Compound 38β).

Sodium (tetradecyl 5-acetamido-5-deoxy-α-D-erythro-L-gluco-2-nonulopyranosid)onate (Compound 39α).

Sodium (hexadecyl 5-acetamido-5-deoxy-α-D-erythro-L-gluco-2-nonulopyranosid)onate (Compound 40α).

5'-O-[sodium (5-acetamido-5-deoxy-α-D-erythro-L-gluco-2-nonulopyranosyl)onate]uridine (Compound 41α).

5'-O-[sodium (5-acetamido-5-deoxy-β-D-erythro-L-gluco-2-nonulopyranosyl )onate ]uridine (Compound 41β).

Example 8

Compound A was glycosidated with 1,2-di-O-acyl-sn-glycerol in the same manner as Example 1(1). After acetylation by the treatment with anhydrous acetic acid in pyridin, α-anomer and β-anomer were separated by silica gel chromatography to give the following compounds.

3-O-[methyl (5-acetamido-3,4,7,8,9-penta-O-acetyl-5-deoxy-α-D-erythro-L-gluco-2-nonulopyranosyl)onate]-1,2-di-O-dodecanoyl-sn-glycerol (Compound 42α).

3-O-[methyl (5-acetamido-3,4,7,8,9-penta-O-acetyl-5-deoxy-β-D-erythro-L-gluco-2-nonulopyranosyl)onate]-1,2-di-O-dodecanoyl-sn-glycerol (Compound 42β).

3-O-[methyl (5-acetamido-3,4,7,8,9-penta-O-acetyl-5-deoxy-α-D-erythro-L-gluco-2-nonulopyranosyl)onate]-1,2-di-O-tetradecanoyl-sn-glycerol (Compound 43α).

3-O-[methyl (5-acetamido-3,4,7,8,9-penta-O-acetyl-5-deoxy-β-D-erythro-L-gluco-2-nonulopyranosyl)onate]-1,2-di-O-tetradecanoyl-sn-glycerol (Compound 43β).

3-O-[methyl (5-acetamido-3,4,7,8,9-penta-O-acetyl-5-deoxy-α-D-erythro-L-gluco-2-nonulopyranosyl)onate]-1,2-di-O-hexadecanoyl-sn-glycerol (Compound 44α).

3-O-[methyl (5-acetamido-3,4,7,8,9-penta-O-acetyl-5-deoxy-β-D-erythro-L-gluco-2-nonulopyranosyl)onate]-1,2-di-O-hexadecanoyl-sn-glycerol (Compound 44β).

The physical data of the said compounds obtained in Examples 5, 6, 7 and 8 were shown in Tables 4, 5, 6 and 7.

Example 9

500 mg of methyl 5-acetamido-4,7,8,9-tetra-O-acetyl-2,3-anhydro-5-deoxy-β-D-erythro-L-gluco-2-nonulopyranosonate, 470 mg of 5-cholesten-3β-ol, 500 mg of anhydrous disodium hydrogenphosphate and 10 ml of dry 1,2-dichloroethane were mixed and stirred. 0.2 ml of trimethylsilyltrifluoromethanesulfonate was added thereto at 5° C. under argon atmosphere. The reaction mixture was stirred for 12 minutes, diluted with benzene, washed with water, saturated sodium hydrogen carbonate and brine, after drying with $Na_2SO_4$, the mixture was evaporated in vacuo to give a crude product. The crude product was purified by silica gel column to give methyl (5-cholesten-3β-yl 5-acetamido-4,7,8,9-tetra-O-acetyl-5-deoxy-D-erythro-β-L-gluco-2-nonulopyranosid)onate (37% yield). The resulting product was deacetylated and then hydrolysis of methyl ester was carried out in the same manner as Example 1(2) and (3) to give Compound 1β. All physical date was identical with that of Compound 1β obtained in Example 1.

Example 10

Sodium salt of 7-hydroxy-4-methylcoumarin (350 mg) and Compound A (500 mg) were stirred in 5 ml of dry dimethylformamide for one hour at room temperature under argon atmosphere. The solvent was removed in vacuo and the residue was partitioned between chloroform and water. The chloroform layer was separated, washed with water and brine, dried ($Na_2SO_4$), and evaporated to give an oil. The oil was purified by silica gel column chromatography and triturated with a mixture of hexane and ethyl acetate to give methyl (4-methylcumarin-7-yl 5-acetamido-4,7,8,9-tetra-O-acetyl-5-deoxy-α-D-erythro-L-gluco-2-nonulopyranosid)onate as a white powder.

The resulting compound was deacetylated in the same manner as Example 1(2). Then after hydrolysis of methyl ester in the same manner as Example 1(3), it was neutralized with cation exchange resin to give 4-methylcumarin-7-yl 5-acetamido-5-deoxy-α-D-erythro-L-gluco-2-nonulopyranosidonic acid (4MU-3β-OH-NeuAc).

Recovery: 90% m.p.: 145°–147° C. $[\alpha]^{25}$: +43.2° (c=1.1, $H_2O$)

IR (KBr): 3400, 1720, 1700, 1603, 1552, 1380, 1360, 1275, 1068, 1015 $cm^{-1}$ Mass (SIMS): m/z 484 (M+H), 308 (M-4MU)

| Elementary Analysis: $C_{21}H_{25}NO_{12}$ | | |
|---|---|---|
| C % | H % | N % |
| Calculated 52.17 | 5.21 | 2.90 |
| Found 52.29 | 4.88 | 2.56 |

Chemical and enzymatic stability and physiological activity of the sialic acid derivatives of the present invention are now described below.

(1) Chemical stability

Chemical stability between the 3-hydroxysialic acid derivative of the present invention (Compounds 2α and 2β) and known sialic acid derivative having no hydroxy group at 3-position. Methyl 6-O-(5-acetamido-3,5-dideoxy-α and β-D-glycero-D-galacto-nonulopyranosylonate-α-D-glucopyranosides were used as comparative compounds with Compound 2α and 2β of the present invention. 250 μg/ml solution (water or 0.01N $H_2SO_4$) of a test compound is stood on a 80° C. water bath. Aliqnots (50 μl) were removed at various times and analyzed by HPLC method using a strong cation exchange resin column. The column eluent was monitored with a UV detector at 205 nm to measure an amount of sialic acid.

Figure 2:
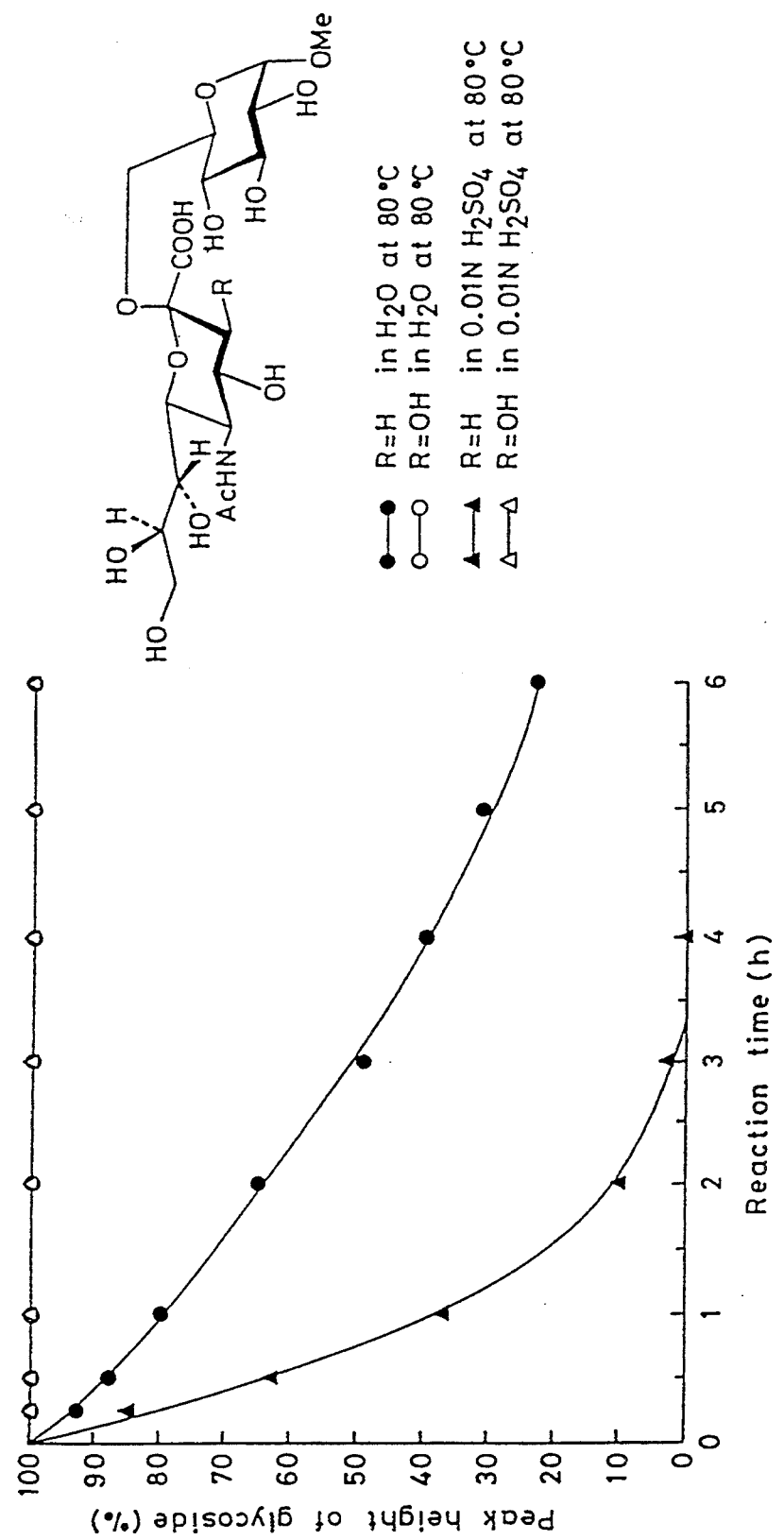

The results are shown in FIGS. 1 and 2.

(2) Enzymatic stability

Sialidase is well known as an enzyme hydrolyzing sialic acid glycoside such as ganglioside or the like. So the stability against sialidases of the compounds of the present invention, which structurally contain 3-hydroxy sialic acid, was studied. In detail, 4MU-3β-OH-NeuAc and 4Mu-NeuAc (no hydroxy group at 3-position) are hydrolyzed with sialidases. In order to analyze the stability against sialidase, released free 4-MU (methylumbellyferon) was determined by measurement of fluorescence emission at 450 nm. Since the substrate specificity of sialidase is different according to the origin, three species of bacterial sialidases and bovine brain sialidase, which can recognize almost all of human brain gangliosides as a substrate, are used in the tests.

The results are shown in Table 8.

(3) Nerve growth stimulating activity

Neuro2a cells (mouse neuroblastoma) purchased from ATCC were cultured in DMEM containing 10% fetal bovine serum (V/V).

Neuro2a cells dispersed by trypsin treatment were diluted with the said medium to $2 \times 10^3$ cells/ml and were pipetted into 24-well plate (1 ml/well). After Neuro2a cells were cultured for 2 days under 95% air and 5% $CO_2$ gas at 37° C., the medium was replaced with 0.9 ml/well of complete serum-free medium and 0.1 ml/well of test compound solutions were added to individual wells. After culturing overnight, five different areas per well were photographed, by using phase-contrast microscope. Cell number with or without neurites (250 μm) of photographs were counted.

The ratio of cell number with neurites to the total cells in control was determined as "1". The ratio to the said control value "1" represents the nerve growth stimulating activity of the test compound (average±S.E.), and results of t-test between a control group and a test group are indicated thus; *: $p<0.05$, : $p<0.01$, *: $p<0.005$.

An example of the results is shown in Table 9.

The difference in the presence or absence of a hydroxy group at 3-position was studied by comparison between compound 13α of the present invention and control compound containing normal sialic acid (no hydroxy group at 3-position). The results are shown in Table 10.

In general, since sialic acid glycosides are not stable, it is hard to deal with them. Especially, α-glycoside, which is natural form, is easy to be hydrolyzed chemically and enzymatically (by sialidase). On the contrary, the compounds of the present invention containing 3-hydroxysialic acid have excellent chemical and enzymatical stability. As shown in FIGS. 1 and 2, α-glycosides and β-glycosides containing structurally normal sialic acid are hydrolyzed with the passing of time. But the compounds of the present invention containing 3-hydroxysialic acid are chemically stable. Even after 6 hours, the compounds of this invention were scarcely decomposed.

Table 8 shows that 4MU-3β-OH-NeuAc which contains 3-hydroxysialic acid was scarcely hydrolyzed by bacterial sialidases and bovine brain sialidase. In addition, 4MU-3β-OH-NeuAc did not inhibit hydrolytic effect of sialidase to 4MU-NeuAc. It is shown by the said results that the compounds of the present invention containing structurally 3-hydroxysialic acid are very stable chemically and enzymatically.

Regarding various sialic acid derivatives, it has been known that they have pharmacological activities such as therapeutic effects of central or peripheral nervous diseases and demyelinating diseases, inhibitory effect against cancer metastasis, antiinflammatory effect and the like. As shown in Tables 9 and 10, the sialic acid derivatives of the present invention having a hydroxy group at 3-position also apparently show the same pharmacological activity, such as nerve growth stimulating activity, as control compound in which 3-position of sialic acid part is hydrogen. In addition, it was confirmed that 3-hydroxysialic acid protected with acetyl group have the nearly same conformation as normal sialic acid by coupling constant in $^1$H-NMR spectrum. This confirmation affirmatively suggests the said test results, i.e. the 3-hydroxysialic acid derivatives as a normal sialic acid.

As shown by the above described results, since the sialic acid derivatives of the present invention having a hydroxy group at 3-position have physiological activities the same as known sialic acid derivatives, they are also useful as drugs for the treatment of central or peripheral nervous diseases, such as dementia, as inhibitors of cancer metastasis, as antiinflammatories and, antirehumatics, and for the treatment of demyelinating diseases.

The compounds of this invention are so stable chemically that it is possible to keep them for long term and very easy to deal with and use them. Additionally, since the sialic acid derivatives of the present invention are not decomposed by a sialidase, the compounds of this invention have longer activities than known physiologically active sialic acid derivatives, which suggests high usefulness of the sialic acid derivatives of the present invention.

TABLE 1

| Compound | Mass (SIMS) | Melting point (°C.) | $[\alpha]^{25}$ (c)* | UV (KBr)-Vmax | | | |
|---|---|---|---|---|---|---|---|
| | | | | NH, OH | ester | amide I | amide II |
| 3α | 624 | | −18.6° (1.3) | 3400 | 1725 | 1630 | 1555 |
| 3β | 624 | | −31.6° (1.3) | 3350 | 1740 | 1650 | 1560 |
| 4α | 680 | | −16.1° (1.1) | 3400 | 1730 | 1630 | 1555 |
| 4β | 680 | | −29.2° (1.0) | 3400 | 1740 | 1640 | 1553 |
| 5α | 736 | | −14.9° (1.1) | 3400 | 1740 | 1655 | 1560 |
| 5β | 736 | | −26.4° (1.1) | 3400 | 1745 | 1645 | 1550 |
| 6α | 792 | | −13.8° (1.2) | 3400 | 1730 | 1633 | 1558 |
| 6β | 792 | | −25.8° (1.3) | 3400 | 1740 | 1648 | 1555 |
| 7α | 848 | 50–51 | −11.7° (2.2) | 3420 | 1730 | 1634 | 1560 |
| 7β | 848 | 96–98 | −25.4° (1.5) | 3400 | 1750 | 1620 | 1580 |
| 8α | 904 | 74–76 | −11.9° (1.6) | 3350 | 1730 | 1640 | 1558 |
| 8β | 904 | 79–81 | −22.6° (1.5) | 3400 | 1740 | 1650 | 1550 |
| 9α | 792 | | −19.8° (1.1) | 3400 | 1740 | 1635 | 1560 |
| 9β | 792 | | −30.5° (1.2) | 3280 | 1700 | 1620 | 1570 |

TABLE 1-continued

| Compound | Mass (SIMS) | Melting point (°C.) | $[\alpha]^{25}$ (c)* | UV (KBr)-Vmax | | |
|---|---|---|---|---|---|---|
| | | | | NH, OH ester | amide I | amide II |
| 10α | 792 | | −16.1° (1.1) | 3400 1730 | 1630 | 1560 |
| 10β | 792 | | −22.2° (1.2) | 3400 1740 | 1645 | 1558 |
| 11α | 764 | | −14.4° (1.1) | 3400 1735 | 1640 | 1558 |
| 11β | 764 | | −25.5° (1.1) | 3400 1740 | 1650 | 1557 |
| 12α | 764 | | −13.1° (1.1) | 3420 1730 | 1635 | 1558 |
| 12β | 764 | | −24.9° (1.1) | 3400 1740 | 1650 | 1560 |

*The specific rotatory power was measured in chloroform.

TABLE 2

| Compound | $^1$H-NMR, δ solvent | O—Ac, N—Ac (s) | OCH$_2$CH$_2$(CH$_2$)$_n$CH$_3$ (t) | OCH$_2$CH$_2$(CH$_2$)$_n$CH$_3$ (m) | OCH$_2$CH$_2$(CH$_2$)$_n$CH$_3$ (m) |
|---|---|---|---|---|---|
| 3α | CD$_3$OD | 2.01 | 0.90 (7.0Hz), 0.90 (7.0Hz) | 1.22–1.42 | 1.51–1.63 |
| 3β | CD$_3$OD | 2.01 | 0.90 (7.0Hz), 0.90 (7.0Hz) | 1.23–1.43 | 1.52–1.64 |
| 4α | CD$_3$OD | 2.01 | 0.90 (7.0Hz), 0.90 (7.0Hz) | 1.22–1.41 | 1.51–1.61 |
| 4β | CD$_3$OD | 2.01 | 0.90 (7.1Hz), 0.90 (7.1Hz) | 1.22–1.43 | 1.53–1.64 |
| 5α | CD$_3$OD | 2.01 | 0.90 (7.0Hz), 0.90 (7.0Hz) | 1.22–1.41 | 1.50–1.62 |
| 5β | CD$_3$OD | 2.01 | 0.90 (7.1Hz), 0.90 (7.1Hz) | 1.22–1.43 | 1.53–1.64 |
| 6α | CD$_3$OD | 2.01 | 0.90 (7.1Hz), 0.90 (7.1Hz) | 1.22–1.41 | 1.51–1.62 |
| 6β | CD$_3$OD | 2.01 | 0.90 (7.0Hz), 0.90 (7.0Hz) | 1.22–1.43 | 1.52–1.65 |
| 7α | CDCl$_3$/CD$_3$OD | 2.03 | 0.89 (7.1Hz), 0.89 (7.1Hz) | 1.21–1.40 | 1.51–1.63 |
| 7β | CDCl$_3$/CD$_3$OD | 2.04 | 0.89 (7.1Hz), 0.89 (7.1Hz) | 1.21–1.41 | 1.53–1.65 |
| 8α | CDCl$_3$/CD$_3$OD | 2.03 | 0.89 (7.0Hz), 0.89 (7.0Hz) | 1.21–1.40 | 1.52–1.65 |
| 8β | CDCl$_3$/CD$_3$OD | 2.04 | 0.89 (7.0Hz), 0.89 (7.0Hz) | 1.21–1.42 | 1.51–1.65 |
| 9α | CD$_3$OD | 2.01 | 0.90 (7.0Hz), 0.90 (7.0Hz) | 1.21–1.42 | 1.51–1.62 |
| 9β | CD$_3$OD | 2.01 | 0.90 (7.1Hz), 0.90 (7.1Hz) | 1.22–1.42 | 1.52–1.63 |
| 10α | CD$_3$OD | 2.01 | 0.90 (7.0Hz), 0.90 (7.0Hz) | 1.21–1.42 | 1.50–1.62 |
| 10β | CD$_3$OD | 2.01 | 0.90 (7.0Hz), 0.90 (7.0Hz) | 1.22–1.44 | 1.52–1.64 |
| 11α | CD$_3$OD | 2.01 | 0.90 (7.1Hz), 0.90 (7.1Hz) | 1.22–1.42 | 1.51–1.62 |
| 11β | CD$_3$OD | 2.01 | 0.90 (7.2Hz), 0.90 (7.2Hz) | 1.22–1.43 | 1.52–1.64 |
| 12α | CD$_3$OD | 2.00 | 0.90 (7.1Hz), 0.90 (7.1Hz) | 1.22–1.42 | 1.51–1.62 |
| 12β | CD$_3$OD | 2.01 | 0,90 (7.1Hz), 0.90 (7.1Hz) | 1.22–1.44 | 1.52–1.65 |

TABLE 3

| Compound | Mass (SIMS) | $[\alpha]^{25}$ (c)* | UV (KBR)-Vmax | | | |
|---|---|---|---|---|---|---|
| | | | NH, OH | ester | amide I | amide II |
| 13α | 568, 590 | −19.0° (1.1) | 3400 | 1725 | 1635 | 1560 |
| 13β | 568 | −42.3° (1.0) | 3400 | 1740 | 1635 | 1550 |
| 14α | 596, 618 | −18.4° (1.2) | 3400 | 1730 | 1640 | 1565 |
| 14β | 596, 618 | −38.6° (1.1) | 3420 | 1740 | 1640 | 1555 |
| 15α | 624, 646 | −16.6° (1.0) | 3400 | 1725 | 1630 | 1555 |
| 15β | 624, 646 | −26.4° (1.1) | 3400 | 1745 | 1645 | 1550 |
| 16α | 652, 674 | −15.3° (1.0) | 3400 | 1730 | 1630 | 1555 |

TABLE 3-continued

| Compound | Mass (SIMS) | $[\alpha]^{25}$ (c)* | UV (KBR)-Vmax | | | |
|---|---|---|---|---|---|---|
| | | | NH, OH | ester | amide I | amide II |
| 16β | 652, 674 | −35.2° (1.1) | 3400 | 1740 | 1640 | 1555 |
| 17α | 680 | −15.9° (1.1) | 3400 | 1730 | 1635 | 1555 |
| 17β | 680 | −34.1° (1.0) | 3400 | 1740 | 1640 | 1560 |
| 18α | 708 | −16.0° (1.0) | 3420 | 1730 | 1630 | 1555 |
| 18β | 708 | −29.1° (1.1) | 3400 | 1730 | 1640 | 1550 |

*The specific rotatory power was measured in methanol.

TABLE 4

| Compound | Mass (SIMS) | Melting point (°C.) | $[\alpha]^{25}$ (c)* | UV (KBr)-vmax | | | |
|---|---|---|---|---|---|---|---|
| | | | | NH, OH | CH | COO$^-$ | C—O |
| 14α | 646, 668 | | −5.9° (1.1) | 3350 | 2925 | 1620 | 1080 |
| 14β | 646, 668 | | −26.3° (1.1) | 3420 | 2920 | 1620 | 1073 |
| 15α | 702, 724 | | −3.7° (1.2) | 3350 | 2920 | 1618 | 1080 |
| 15β | 702, 724 | | −24.5° (1.0) | 3430 | 2920 | 1622 | 1080 |
| 16α | 758, 780 | | −3.1° (1.0) | 3400 | 2915 | 1625 | 1080 |
| 16β | 758, 780 | | −22.7° (1.0) | 3420 | 2920 | 1622 | 1080 |
| 17α | 814, 836 | | −2.6° (1.1) | 3300 | 2915 | 1612 | 1060 |
| 17β | 814, 836 | | −21.0° (1.1) | 3450 | 2920 | 1622 | 1078 |
| 18α | 870, 892 | 139–141 | −2.9° (1.0) | 3350 | 2915 | 1615 | 1080 |
| 18β | 870, 892 | 169–171 | −19.2° (1.1) | 3430 | 2920 | 1625 | 1080 |
| 19α | 926, 948 | 183–185 | −2.2° (1.1) | 3300 | 2910 | 1615 | 1075 |
| 19β | 926, 948 | 161–163 | −17.0° (1.1) | 3400 | 2915 | 1622 | 1078 |
| 20α | 814, 836 | | −20.4° (1.0) | 3400 | 2920 | 1615 | 1078 |
| 20β | 814, 836 | | −32.4° (1.1) | 3400 | 2920 | 1630 | 1080 |
| 21α | 814, 836 | | −13.6° (1.0) | 3450 | 2920 | 1620 | 1070 |
| 21β | 814, 836 | | −25.9° (1.0) | 3400 | 2910 | 1620 | 1075 |
| 22α | 786, 808 | | −4.5° (1.1) | 3380 | 2920 | 1620 | 1070 |
| 22β | 786, 808 | | −22.7° (1.0) | 3400 | 2920 | 1625 | 1075 |
| 23α | 786, 808 | | −4.9° (1.1) | 3400 | 2920 | 1620 | 1070 |
| 23β | 786, 808 | | −22.4° (1.1) | 3400 | 2920 | 1625 | 1072 |

*The specific rotatory power was measured in methanol/chloroform (1/1).

TABLE 5

| Compound | $^1$H-NMR, δ solvent | N—Ac (s) | OCH$_2$CH$_2$(CH$_2$)$_n$CH$_3$ (t) | OCH$_2$CH$_2$(CH$_2$)$_n$CH$_3$ (m) | OCH$_2$CH$_2$(CH$_2$)$_n$CH$_3$ (m) | OCH$_2$CH$_2$(CH$_2$)$_n$CH$_3$, glycerol & Neu5Ac (m) |
| --- | --- | --- | --- | --- | --- | --- |
| 14α | CD$_3$OD | 2.00 | 0.90 (7.0Hz), 0.90 (7.0Hz) | 1.22–1.41 | 1.49–1.61 | 3.36–3.90 |
| 14β | CD$_3$OD | 1.99 | 0.90 (7.2Hz), 0.90 (7.2Hz) | 1.22–1.42 | 1.52–1.65 | 3.38–4.07 |
| 15α | CD$_3$OD | 2.00 | 0.90 (7.1Hz), 0.90 (7.1Hz) | 1.22–1.41 | 1.49–1.61 | 3.36–3.90 |
| 15β | CD$_3$OD | 1.99 | 0.90 (7.2Hz), 0.90 (7.2Hz) | 1.22–1.42 | 1.52–1.65 | 3.38–4.06 |
| 16α | CD$_3$OD | 2.00 | 0.90 (7.2Hz), 0.90 (7.2Hz) | 1.22–1.41 | 1.49–1.61 | 3.36–3.90 |
| 16β | CD$_3$OD | 1.98 | 0.90 (7.2Hz), 0.90 (7.2Hz) | 1.22–1.42 | 1.52–1.65 | 3.37–4.06 |
| 17α | CD$_3$OD | 2.00 | 0.90 (7.0Hz), 0.90 (7.0Hz) | 1.21–1.41 | 1.49–1.61 | 3.37–3.90 |
| 17β | CD$_3$OD | 1.99 | 0.90 (7.2Hz), 0.90 (7.2Hz) | 1.21–1.43 | 1.52–1.65 | 3.38–4.06 |
| 18α | CDCl$_3$ | 2.00 | 0.90 (6.9Hz), 0.90 (6.9Hz) | 1.22–1.41 | 1.48–1.61 | 3.36–3.90 |
| 18β | CDCl$_3$/CD$_3$OD | 2.03 | 0.89 (7.0Hz), 0.89 (7.0Hz) | 1.18–1.44 | 1.52–1.67 | 3.43–4.01 |
| 19α | CDCl$_3$/CD$_3$OD | 2.03 | 0.89 (6.8Hz), 0.89 (6.8Hz) | 1.19–1.40 | 1.51–1.63 | 3.43–3.97 |
| 19β | CDCl$_3$/CD$_3$OD | 2.04 | 0.89 (6.8Hz), 0.89 (6.8Hz) | 1.18–1.45 | 1.53–1.67 | 3.42–4.04 |
| 20α | CD$_3$OD | 2.00 | 0.90 (6.9Hz), 0.90 (6.9Hz) | 1.21–1.41 | 1.49–1.61 | 3.35–3.91 |
| 20β | CD$_3$OD | 1.99 | 0.90 (6.9Hz), 0.90 (6.9Hz) | 1.21–1.42 | 1.51–1.63 | 3.40–4.05 |
| 21α | CD$_3$OD | 2.00 | 0.90 (6.8Hz), 0.90 (6.8Hz) | 1.22–1.42 | 1.49–1.62 | 3.36–3.91 |
| 21β | CD$_3$OD | 1.99 | 0.90 (7.1Hz), 0.90 (7.1Hz) | 1.20–1.42 | 1.51–1.65 | 3.38–4.07 |
| 22α | CD$_3$OD | 2.00 | 0.90 (7.0Hz), 0.90 (7.0Hz) | 1.22–1.41 | 1.49–1.62 | 3.36–3.91 |
| 22β | CD$_3$OD | 1.98 | 0.90 (6.9Hz), 0.90 (6.9Hz) | 1.21–1.42 | 1.52–1.65 | 3.38–4.07 |
| 23α | CD$_3$OD | 2.00 | 0.90 (6.6Hz), 0.90 (6.6Hz) | 1.21–1.42 | 1.49–1.62 | 3.37–3.92 |
| 23β | CD$_3$OD | 1.99 | 0.90 (6.7Hz), 0.90 (6.7Hz) | 1.20–1.42 | 1.52–1.65 | 3.38–4.07 |

TABLE 6

| Compound | Mass (SIMS) | $[\alpha]^{25}$ (c)* | UV (KBR)-vmax NH, OH | CH | COO$^-$ | C—O |
| --- | --- | --- | --- | --- | --- | --- |
| 33α | 590 | −14.4° (1.0) | 3380 | 2910 | 1615 | 1075 |
| 33β | 590 | −36.4° (1.1) | 3400 | 2910 | 1620 | 1072 |
| 34α | 618 | −14.1° (1.2) | 3400 | 2915 | 1620 | 1075 |
| 34β | 618 | −35.1° (1.1) | 3380 | 2920 | 1620 | 1070 |
| 35α | 646 | −12.7° (1.1) | 3400 | 2910 | 1620 | 1070 |
| 35β | 646 | −33.5° (1.1) | 3380 | 2915 | 1620 | 1065 |
| 36α | 674 | −12.3° (1.3) | 3400 | 2910 | 1620 | 1075 |
| 36β | 674 | −31.9° (1.0) | 3400 | 2910 | 1620 | 1070 |
| 37α | 702 | −11.5° (1.2) | 3400 | 2910 | 1620 | 1072 |
| 37β | 702 | −31.2° (1.0) | 3400 | 2910 | 1620 | 1075 |
| 38α | 730 | −10.5° (0.5) | 3400 | 2910 | 1622 | 1075 |
| 38β | 730 | −28.5° (0.5) | 3400 | 2910 | 1620 | 1075 |

*The specific rotatory power was measured in methanol/chloroform (1/1).

TABLE 7

| Compound | Mass (SIMS or EI) | Melting point (°C.) | $[\alpha]^{25}$ (c)* | UV (KBr)-vmax NH, OH | COO | Amide I | Amide II |
| --- | --- | --- | --- | --- | --- | --- | --- |
| 19α | 522 | 126–128 | −21.6° (1.1)$^a$ | 3430 | 1730 | 1635 | 1560 |
| 20α | 550 | 131–133 | −20.1° (1.1)$^a$ | 3400 | 1740 | 1640 | 1560 |
| 21α | 552 | | −21.1° (1.0)$^c$ | 3400 | 1680 | | 1550 |
| 21β | 552 | | −11.6° (1.1)$^c$ | 3400 | 1680 | | 1550 |
| 39α | 544 | | −16.6° (1.0)$^a$ | 3450 | | 1620 | 1555 |
| 40α | 572 | | −13.9° (1.1)$^a$ | 3400 | | 1620 | 1560 |
| 41α | 574 | | −18.6° (1.1)$^c$ | 3350 | 1680 | 1620 | 1555 |
| 41β | 574 | | −11.1° (1.1)$^c$ | 3400 | 1680 | 1620 | 1550 |
| 42α | 987 | | +1.1° (1.3)$^b$ | 3250 | 1740 | 1660 | 1540 |
| 42β | 988 | | −9.0° (1.0)$^b$ | 3370 | 1740 | 1660 | 1540 |
| 43α | 1044 | 64–66 | +1.8° (1.2)$^b$ | 3230 | 1750 | 1655 | 1560 |
| 43β | 1044 | 67–69 | −8.3° (2.1)$^b$ | 3370 | 1740 | 1660 | 1540 |
| 44α | 1100 | 80–82 | +2.3° (1.1)$^b$ | 3245 | 1745 | 1650 | 1550 |
| 44β | 1100 | 76–78 | −8.6° (1.1)$^b$ | 3390 | 1745 | 1660 | 1532 |

*The specific rotatory power was measured in methanol$^a$, chloroform$^b$ or water$^c$.

TABLE 8

| Sialidase Origin | Sustrate (addition: +, non-addition: −) 4MU-3-β-OH—Neu5Ac | 4MU—Neu5Ac | 4-MU liberated nmol |
| --- | --- | --- | --- |
| *Arthrobacter ureafaciens* (bacterium) | + | + | 15.1 |
| | − | + | 15.8 |
| | + | − | 0.4 |
| *Clostridium pefringens* (bacterium) | + | + | 19.1 |
| | − | + | 19.7 |
| | + | − | 0.5 |
| *Vibrio choleras* (bacterium) | + | + | 16.0 |
| | − | + | 17.0 |
| | + | − | 0.9 |
| Bovine brain | + | + | 7.4 |
| | − | + | 6.6 |
| | + | − | 0.5 |

TABLE 9

| Test compound | Concentration (mM) | Ratio of Neuro2a cells with neurites |
| --- | --- | --- |
| Compound 23α | 10.0 | 4.11 ± 0.62* |
| Compound 23β | 10.0 | 4.68 ± 0.47** |

TABLE 9-continued

| Test compound | Concentration (mM) | Ratio of Neuro2a cells with neurites |
|---|---|---|
| Compound 24α | 0.25 | 3.33 ± 0.42* |
| Compound 24β | 0.25 | 3.88 ± 0.31** |
| Compound 25α | 0.50 | 5.09 ± 0.40** |
| Compound 25β | 1.00 | 4.44 ± 0.75* |
| Compound 26α | 1.25 | 3.18 ± 0.60* |
| Compound 26β | 1.25 | 3.21 ± 0.25** |
| Compound 27α | 1.25 | 2.67 ± 0.31** |
| Compound 27β | 1.25 | 2.81 ± 0.55* |
| Compound 28α | 1.25 | 2.02 ± 0.24* |
| Compound 28β | 2.50 | 1.71 ± 0.27 |

TABLE 10

| Test compound | Concentration (mM) | Ratio of Neuro2a cells with neurites |
|---|---|---|
| Compound 13α | 10 | 2.48 ± 0.38* |
| | 50 | 3.09 ± 0.43** |
| | 100 | 3.32 ± 0.38** |
| | 200 | 3.02 ± 0.21*** |
| normal sialic acid corresponding to Compound 13α | 10 | 2.27 ± 0.34* |
| | 50 | 2.37 ± 0.30** |
| | 100 | 2.70 ± 0.17*** |
| | 200 | 3.42 ± 0.22*** |

What is claimed is:

1. A sialic acid compound of the formula

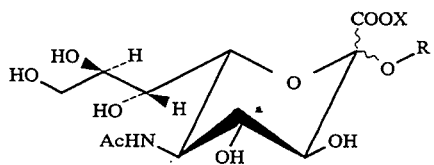

wherein X is hydrogen, a $C_{1-4}$ alkyl or benzyl group, Ac is acetyl,

R is alkyl, glucose, cholesterol, alkylglycerol dialkylglycerol, diacylglycerol or uridine;

or a pharmaceutically acceptable salt thereof.

2. A sialic acid compound of the formula

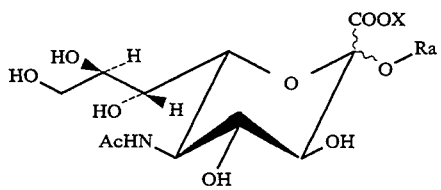

wherein X is hydrogen, a $C_{1-4}$ alkyl or benzyl group, Ac is acetyl and Ra is alkylglycerol;

or a pharmaceutically acceptable salt thereof.

3. A sialic acid compound of the formula

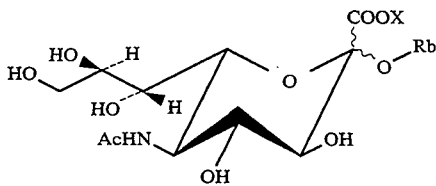

wherein X is hydrogen, a $C_{1-4}$ alkyl or benzyl group, Ac is acetyl and Rb is dialkylglycerol;

or a pharmaceutically acceptable salt thereof.

4. A sialic acid compound of the formula

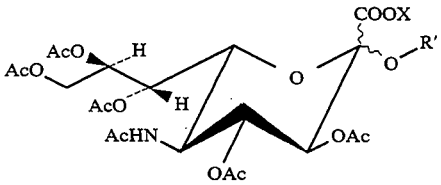

wherein X is hydrogen, a $C_{1-4}$ alkyl or benzyl group, Ac is acetyl and R' is diacylglycerol;

or a pharmaceutically acceptable salt thereof.

5. The compound according to any one of claims 1-4, wherein X is hydrogen.

6. The compound according to any one of claims 1-4, wherein X is a $C_{1-4}$ alkyl group.

7. The compound according to any one of claims 1-4, wherein the pharmaceutically acceptable salt is an alkali metal salt.

8. The compound according to claim 2, wherein the alkali metal is sodium.

9. The compound according to any one of claims 1-4, which is an α-anomer.

10. The compound according to any one of claims 1-4, which is a β-anomer.

* * * * *